United States Patent
Asada et al.

(10) Patent No.: US 8,517,927 B2
(45) Date of Patent: Aug. 27, 2013

(54) MEDICAL INSTRUMENT (75) Inventors: Daisuke Asada, Hachioji (JP); Sho Nakajima, Hachioji (JP); Hitoshi Karasawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 405 days.

(21) Appl. No.: 12/842,668

(22) Filed: Jul. 23, 2010

(65) Prior Publication Data

US 2011/0046445 A1 Feb. 24, 2011

Related U.S. Application Data (63) Continuation of application No. PCT/JP2009/066406, filed on Sep. 18, 2009.

(30) Foreign Application Priority Data

Mar. 25, 2009 (JP) .................................. 2009-074436

(51) Int. Cl.
*A61B 1/12* (2006.01)

(52) U.S. Cl.
USPC ........... 600/157; 600/121; 600/122; 600/170; 600/173; 600/176

(58) Field of Classification Search
USPC ................. 600/109, 121, 122, 127, 155–158, 600/169, 174; 348/65
See application file for complete search history.

(56) References Cited

U.S. PATENT DOCUMENTS

| 5,191,878 | A | 3/1993 | Iida et al. |
| 5,339,800 | A | 8/1994 | Wiita et al. |
| 5,464,008 | A | 11/1995 | Kim |
| 8,088,065 | B2 * | 1/2012 | Karasawa et al. ............ 600/122 |
| 8,237,782 | B2 * | 8/2012 | Karasawa et al. ............ 600/122 |
| 2003/0214580 | A1 * | 11/2003 | Iddan ............................ 348/81 |

(Continued)

FOREIGN PATENT DOCUMENTS

| JP | H1-59101 | 4/1989 |
| JP | 03-048086 | 3/1991 |

(Continued)

OTHER PUBLICATIONS

Extended Supplementary European Search Report dated Oct. 24, 2012 corresponding to Application No. / Patent No. JP 09842306.4-2319 / 2412288 PCT/JP2009066406.

(Continued)

*Primary Examiner* — Matthew J Kasztejna
*Assistant Examiner* — Kevin G Barry, III
(74) *Attorney, Agent, or Firm* — Scully, Scott, Murphy & Presser, P.C.

(57) ABSTRACT

A medical instrument includes: an image pickup unit incorporated in a medical instrument body for picking up an image of the subject to be examined from an observation window; an airflow generating unit provided rotatably with respect to the medical instrument body so as to cover the image pickup unit by a covering unit having an opening formed therein, the airflow generating unit being configured to generate an airflow for preventing adherents from sticking to the observation window, by rotation of the covering unit; a fixing unit for indwelling and fixing the medical instrument body inside the subject to be examined; and a drive unit incorporated in the medical instrument body, for driving the airflow generation unit.

2 Claims, 11 Drawing Sheets

(56) References Cited

U.S. PATENT DOCUMENTS

| | | | |
|---|---|---|---|
| 2006/0063974 A1* | 3/2006 | Uchiyama et al. | 600/114 |
| 2006/0169293 A1* | 8/2006 | Yokoi et al. | 600/160 |
| 2007/0106319 A1* | 5/2007 | Au et al. | 606/191 |
| 2008/0081948 A1* | 4/2008 | Weisenburgh et al. | 600/121 |
| 2008/0309758 A1 | 12/2008 | Karasawa et al. | |
| 2008/0312500 A1 | 12/2008 | Asada et al. | |

FOREIGN PATENT DOCUMENTS

| | | |
|---|---|---|
| JP | 05-103748 | 4/1993 |
| JP | 08-029699 | 2/1996 |
| JP | 2004-254989 | 9/2004 |
| JP | 2005-134075 | 5/2005 |
| JP | 2005-176908 | 7/2005 |
| JP | 2006-75308 | 3/2006 |
| JP | 2007-14634 | 1/2007 |
| JP | 2007-20951 | 2/2007 |
| JP | 2008-119364 | 5/2008 |
| JP | 2008-253634 | 10/2008 |
| JP | 2008-289563 | 12/2008 |
| JP | 2008-289564 | 12/2008 |

OTHER PUBLICATIONS

European Search Report dated Oct. 24, 2012 from corresponding European Patent Application No. EP 09 84 2306.4.

* cited by examiner

MEDICAL INSTRUMENT

CROSS REFERENCE TO RELATED APPLICATION

This application is a continuation application of PCT/JP2009/066406 filed on Sep. 18, 2009 and claims benefit of Japanese Application No. 2009-074436 filed in Japan on Mar. 25, 2009, the entire contents of which are incorporated herein by this reference.

BACKGROUND OF THE INVENTION

1. Field of the Invention

The present invention relates to a medical instrument provided with image pickup means for observing the interior of the body of a patient.

2. Description of the Related Art

As is generally known, endoscope apparatuses, which are medical instruments, are provided with an image pickup apparatus which is image pickup means, designed to be introduced into the body cavity of a patient and carry out various kinds of inspections and treatment or the like of affected areas in the body based on observed images photographed by the image pickup apparatus. Examples of such endoscopes include those introduced into digestive organs such as esophagus, stomach, large intestine, duodenum, which are tube cavities in the body from the oral cavity or anus and those introduced into the abdominal cavity from the vicinity of the umbilical region by puncturing through the body wall.

In a medical endoscope apparatus, smear in the body such as mucous membrane, dirt, blood may stick to an observation window of the image pickup apparatus or moisture may stick to the observation window of the image pickup apparatus due to a highly humid use environment in the body, causing window fogging. Thus, such adherents may degrade visibility and prevent clear photographed images from being acquired. Therefore, various proposals to remove adherents stuck to the observation window of the image pickup apparatus have been conventionally presented.

For example, Japanese Patent Application Laid-Open Publication No. 8-29699 discloses an image scope provided with a wiper that wipes dirt off the outer surface of an objective lens. Furthermore, for example, Japanese Patent Application Laid-Open Publication No. 5-103748 discloses a catheter apparatus for endoscopy provided with a catheter body in which an endoscope whose observation window and channel opening are exposed to the distal end portion is inserted.

The conventional catheter apparatus for endoscopy forms a shielding member at the distal end portion of the catheter body for shielding at least part of the opening of the channel of the distal end portion of the endoscope or the like and is also provided with a locking mechanism as restricting means for restricting relative rotation between the endoscope and the catheter body and discloses a technique capable of opening/closing the opening of the channel as required. Furthermore, a wiping member such as buff is provided on the back of the shielding member so as to allow the wiping member to wipe away dirt or the like stuck to the observation window and illumination window of the endoscope.

SUMMARY OF THE INVENTION

A medical instrument according to an embodiment of the present invention is medical instrument for observing an interior of a subject to be examined, provided with: an image pickup unit incorporated in a medical instrument body, for picking up an image of the subject to be examined from an observation window; an airflow generating unit provided rotatably with respect to the medical instrument body so as to cover the image pickup unit by a covering unit having an opening formed therein, the airflow generating unit being configured to generate an airflow for preventing adherents from sticking to the observation window, by means of rotation of the covering unit; a fixing unit for indwelling and fixing the medical instrument body inside the subject to be examined; and a drive unit incorporated in the medical instrument body, for driving the airflow generation unit

DETAILED DESCRIPTION OF THE PREFERRED EMBODIMENTS

Hereinafter, embodiments of the present invention will be described based on the accompanying drawings. A medical instrument provided with image pickup means used during laparoscopic surgery will be described in the following descriptions as an example.

(First Embodiment)

First, a camera set up in the abdominal cavity which is a medical instrument of the present invention used for laparoscopic surgery will be described below based on FIG. 1 to FIG. 5.

Figure 1:
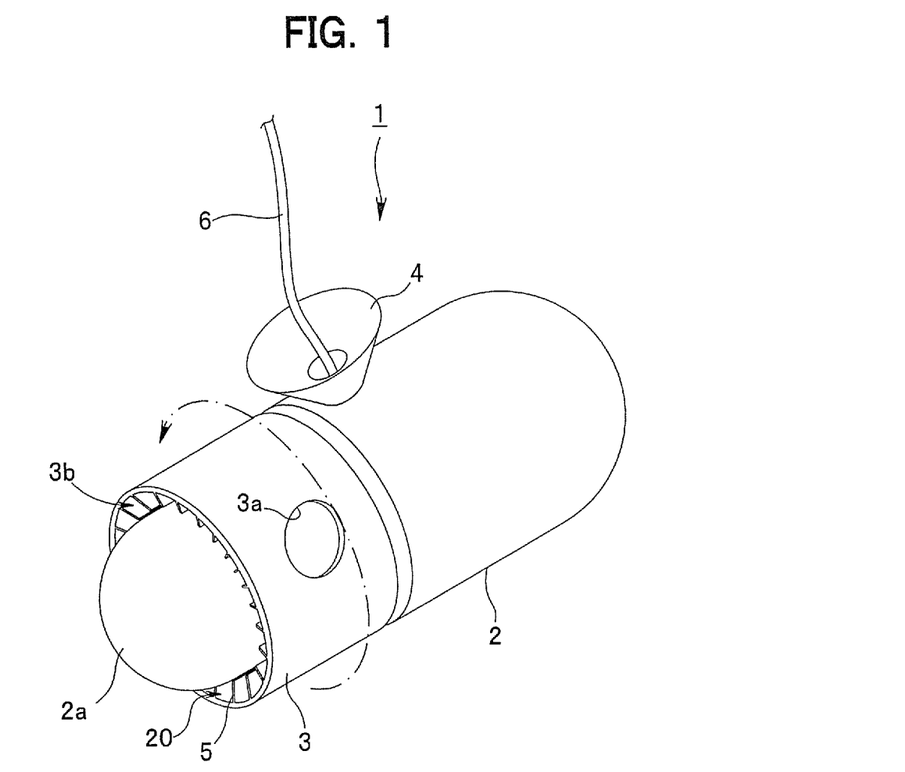
FIG. 1 is a perspective view illustrating a configuration of a camera set up in the abdominal cavity according to a first embodiment.
Figure 2:
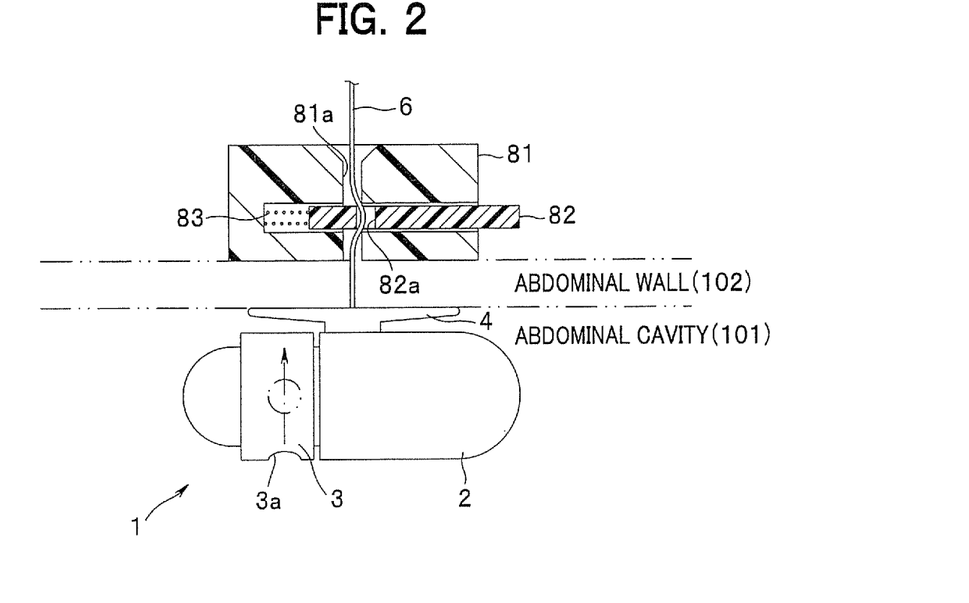
FIG. 2 is a partial cross-sectional view illustrating the camera set up in the abdominal cavity according to the first embodiment installed in the abdominal cavity.
Figure 3:
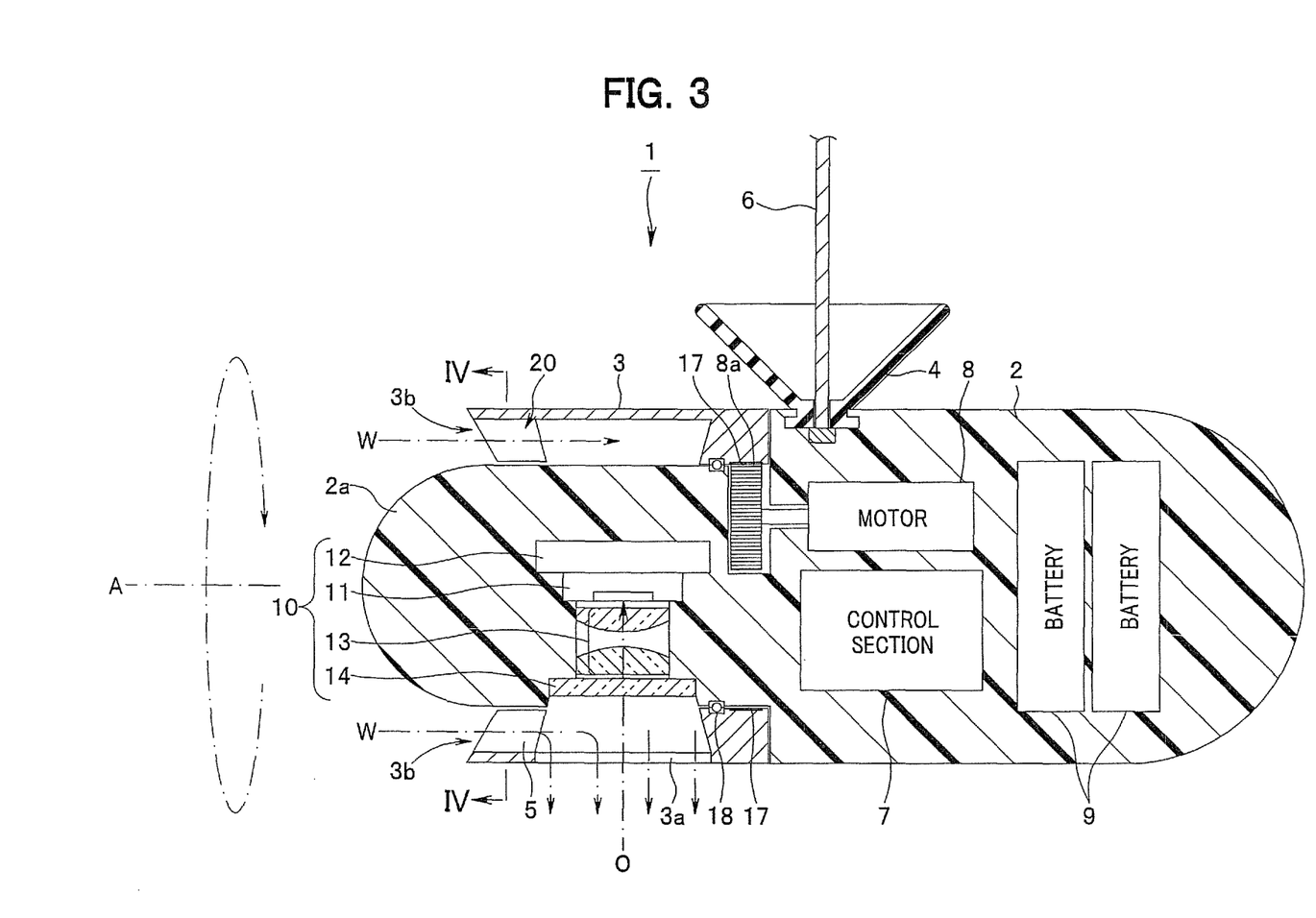
FIG. 3 is a cross-sectional view illustrating a configuration of the camera set up in the abdominal cavity according to the first embodiment.

As shown in FIG. 1 to FIG. 3, the camera set up in the abdominal cavity (hereinafter simply referred to as "camera") 1 which is a medical instrument of the present embodiment is configured by mainly including a camera body 2 which is a capsule-shaped medical instrument body that incorporates image pickup means (image pickup section), a rotary cover 3 which is airflow generation covering means (airflow generation covering section) rotatably disposed on the outer circumferential portion on one end side of the camera body 2, a suction cup 4 which is fixing means engaged with the camera body 2 and constitutes an abdominal wall fixing section and a wire 6 that extends from the center of the suction cup 4. The camera 1 is provided with an illumination unit (not shown) that irradiates a subject (subject to be examined) with illuminating light.

The camera 1 of the present embodiment is used for laparoscopic surgery and used to photograph a region to be treated when treating an organ in the abdominal cavity 101 which is one of the body cavities of the patient.

First, the camera 1 is introduced into the abdominal cavity 101 of the patient via a trocar (not shown) punctured into the abdominal wall 102. The wire 6 of the camera 1 is hooked onto a puncture needle (not shown) or the like punctured into the abdominal cavity 101 and the wire 6 is pulled out of the body penetrating the abdominal wall 102.

Next, the wire 6 of the camera 1 is passed through a hole 81a of a fixing unit 81 prepared on the abdomen side of the patient and pulled toward the abdominal wall 102 side. The camera 1 is then lifted to come closer to the abdominal wall 102 and the wire 6 is pulled until the suction cup 4 sticks to the inner surface of the abdominal wall 102. Thus, the camera 1 is left indwelling and fixed in the abdominal cavity 101 by the suction cup 4 sticking to the abdominal wall 102.

The fixing unit 81 is provided with a fixing lever 82 that fixes the wire 6 of the camera 1 outside the body. A hole 82a through which the wire 6 passes is formed at some midpoint of the fixing lever 82 and the fixing lever 82 is biased toward one direction of the fixing unit 81 by a spring 83 provided in the fixing unit 81 so that the position of the hole 82a is deviated from the position of the hole 81a of the fixing unit 81.

That is, when the user pushes the fixing lever 82 into the fixing unit 81 against the urging force of the spring 83 up to a position where the hole 81a of the fixing unit 81 substantially coincides with the hole 82a of the fixing lever 82, the user can easily pull the wire 6. When the user stops pushing the fixing lever 82 into the fixing unit 81, the fixing lever 82 slides under the urging force of the spring 83.

This produces a difference between the position of the hole 81a of the fixing unit 81 and the position of the hole 82a of the fixing lever 82 and the wire 6 of the camera 1 that passes through the holes 81a and 82a is caught and fixed in the fixing unit 81. Thus, as shown in FIG. 2, the camera 1 is left indwelling and fixed stably with the suction cup 4 which is an abdominal wall fixing section sticking to the abdominal wall 102 in the abdominal cavity 101.

Figure 4:
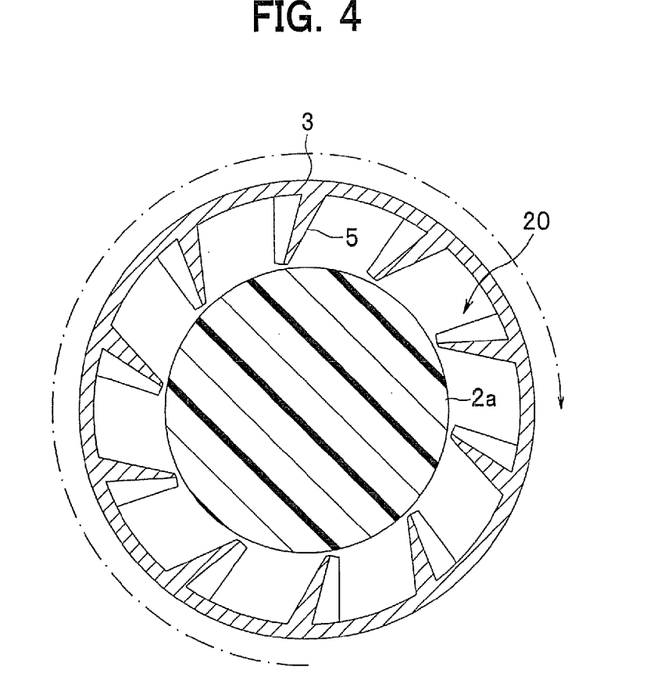
FIG. 4 is a cross-sectional view along the line IV-IV of FIG. 3 according to the first embodiment.

Next, as described above, a more specific configuration of the camera 1 left indwelling and fixed in the abdominal cavity 101 will be described in detail here using FIG. 3 and FIG. 4.

The camera body 2 of the camera 1 is internally provided with a control section 7 which is control means making up a controller, a motor 8 which is drive means (drive source) making up a drive section, two batteries 9 which is a power supply section and an image pickup unit 10 which is image pickup means making up an image pickup section.

The control section 7 is provided with a transmitter that transmits an image signal photoelectrically converted by the image pickup unit 10 to an external device and a receiver that receives a drive instruction signal of the motor 8 transmitted from the external device (both are not shown) and drives/controls the motor 8 according to the drive instruction signal received.

Furthermore, the two batteries 9 make up a power supply section for driving the control section 7, the motor 8, the image pickup unit 10 and the illumination unit (not shown). The two batteries 9 are electrically connected to the control section 7 via an electric cable (not shown) for a power supply and the control section 7 is connected with a communication cable (not shown) for a power supply and for sending/receiving signals individually connected to the motor 8, the image pickup unit 10 or the like.

Furthermore, the image pickup unit 10 is configured by including a solid image pickup device 11 such as CCD, CMOS, an image pickup substrate 12 on which the solid image pickup device 11 is mounted, a plurality of objective lenses 13 and a cover lens 14 that serves as an observation window. The image pickup unit 10 outputs a photoelectrically converted image signal to the control section 7. The control section 7 then transmits the image signal from an internal transmitter to a camera control unit (CCU) which is an external device (not shown). An image photographed by the image pickup unit 10 is subjected to image processing by the CCU and displayed on an external monitor (not shown).

The camera body 2 has a small diameter end 2a which forms a substantially half end thereof with a small diameter. The small diameter end 2a incorporates the image pickup unit 10. The aforementioned rotary cover 3 is rotatably held and disposed on the outer circumferential portion of the small diameter end 2a via a bearing 18 around a longitudinal central axis A of the camera body 2. The cover lens 14 of the image pickup unit 10 is disposed at a portion of the outer perimeter on the underside of the small diameter end 2a so as to be exposed at the bottom of the camera body 2, that is, opposite to the suction cup 4.

Thus, the rotary cover 3 rotatably disposed on the small diameter end 2a of the camera body 2 has a cylindrical shape and an opening 3a is formed therein which serves as a circular airflow outlet for exposing the cover lens 14 of the image pickup unit 10. Furthermore, a gear groove 17 is formed in the inner perimeter of one (inside) end of the rotary cover 3 which meshes with a spur gear 8a of the motor 8 incorporated in the camera body 2.

That is, the rotary cover 3 rotates around the outer perimeter of the small diameter end 2a of the camera body 2, that is, around the longitudinal central axis A of the camera body 2 by the torque transmitted from the gear 8a driven by the motor 8. Furthermore, a plurality of fan blades 5 are provided outside the range of field of view (image-pickup field of view) of the image pickup unit 10 on the inner perimeter at the other (outside) end of the rotary cover 3 as shown in FIG. 4. That is, the rotary cover 3 is provided with a multi-bladed fan 20 made up of the plurality of fan blades 5 for generating an airflow in the inner perimeter at the other end.

Furthermore, a space is formed so as to separate the inner perimeter surface between the one end of the rotary cover 3 rotatably held by the bearing 18 and the other end provided with the plurality of fan blades 5 from the surface of the cover lens 14 of the image pickup unit 10 and the outer surface of the small diameter end 2a of the camera body 2 by a predetermined distance. The plurality of fan blades 5 extend in the inner circumferential direction of the rotary cover 3 so as not to contact the outer surface of the small diameter end 2a of the camera body 2.

The camera 1 of the present embodiment configured as shown above is introduced into the abdominal cavity 101 as shown in FIG. 2, and in an operating condition in which the camera 1 is left indwelling and fixed in the abdominal wall 102, the motor 8 is driven through wireless operation from outside and the gear 8a rotates. The rotary cover 3 that meshes with the gear 8a then rotates around the outer perimeter of the small diameter end 2a of the camera body 2.

Figure 5:
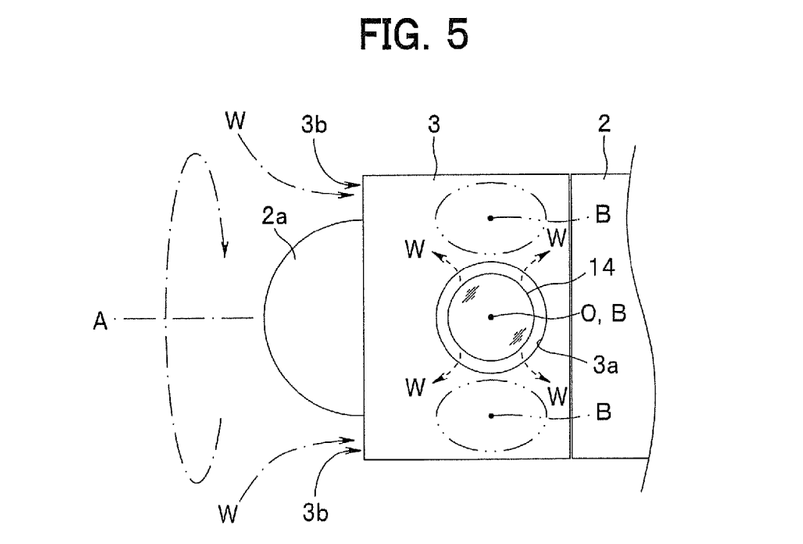
FIG. 5 is a plan view illustrating a state in which the rotary cover has rotated around the outer perimeter of the camera body according to the first embodiment.

In this case, the opening 3a formed in the rotary cover 3 moves along the outer circumferential portion of the small diameter end 2a of the camera body 2 as shown in FIG. 5. Furthermore, the rotary cover 3 moves around the outer perimeter of the camera body 2 so as to pass through a position at which the center position B which is the center of the opening of the opening 3a coincides with an optical axis O of a subject (subject to be examined) image photographed by the image pickup unit 10.

Thus, the camera 1 left indwelling in the body (abdominal cavity 101) is controlled so that the rotary cover 3 always rotates around the outer perimeter of the camera body 2 when photographing a subject (subject to be examined) such as an organ in the body (abdominal cavity 101).

In the camera 1, the control section 7 controls the drive of the motor 8 that rotates the rotary cover 3 so that the timing at which the opening 3a of the rotary cover 3 moves to a position that aligns with the cover lens 14 of the image pickup unit 10 matches the timing of the frame rate of the image pickup unit 10.

That is, the control section 7 controls the drive of the motor 8 so that the opening 3a of the rotary cover 3 matches the cover lens 14 of the image pickup unit 10 in synchronization with the timing at which the image pickup unit 10 of the camera 1 captures a subject (subject to be examined) image when the rotary cover 3 rotates. As described above, this timing is the timing at which the center position B of the opening 3a of the rotary cover 3 matches the optical axis O of the subject (subject to be examined) image that impinges on the image pickup unit 10.

When, for example, the frame rate of the image pickup unit 10 is 60 fps, the control section 7 performs control such that the number of revolutions when the rotary cover 3 rotates around the outer perimeter of the camera body 2 becomes 60 revolutions/sec so that the center position B of the opening 3a of the rotary cover 3 matches the optical axis O of the subject (subject to be examined) image that impinges on the image pickup unit 10 in synchronization with the frame rate, that is, timing at which an image is captured.

Furthermore, when the rotary cover 3 rotates, an airflow W is generated by the multi-bladed fan 20 made up of the plurality of fan blades 5 provided at the inner perimeter edge outside the range of field of view (image-pickup field of view) of the image pickup unit 10. To be more specific, when the rotary cover 3 rotates, here the opening on the other end side (outside) provided with the plurality of fan blades 5 serves as a suction inlet 3b which is an inlet port and the gas in the abdominal cavity 101 is suctioned between the inner circumferential face which is inside and the outer circumferential face of the small diameter end 2a of the camera body 2. The suctioned gas is always exhausted from the opening 3a of the rotary cover 3 to the abdominal cavity 101 which is outside.

A wind force of the airflow W generated in this case blows off dirt by blood, mucous membrane or the like scattering from the treated diseased part and smoke or the like generated during treatment of the diseased part using a high frequency treatment device, and can thereby prevent dirt or the like from sticking to the surface of the cover lens 14 of the image pickup unit 10. Especially the wind force of the airflow W generated prevents the surface of the cover lens 14 from fogging.

As described above, the camera 1 of the present embodiment is configured such that in synchronization with the moment (timing) at which the image pickup unit 10 captures the subject (subject to be examined) image, the opening 3a of the rotary cover 3 moves to a position matching the position of the cover lens 14 of the image pickup unit 10 and the cover lens 14 is exposed by the opening 3a of the rotary cover 3. Thus, the camera 1 shortens the time during which the cover lens 14 of the image pickup unit 10 is exposed, blows off dirt by blood, mucous membrane or the like scattering from the treated diseased part and smoke or the like generated during treatment of the diseased part using a high frequency treatment device, and can thereby prevent dirt or the like from sticking to the surface of the cover lens 14 of the image pickup unit 10.

Furthermore, since the suctioned gas forms a so-called air curtain and is exhausted from the opening 3a of the rotary cover 3, the wind force blows off dirt by blood, mucous membrane or the like scattering from the treated diseased part, smoke or the like generated during treatment of the diseased part using a high frequency treatment device, thus preventing dirt from approaching the surface of the cover lens 14, thereby preventing the lens from fogging or dirt or the like from sticking to the surface of the cover lens 14. The rotary cover 3 is always driven to rotate when the camera 1 is driven, that is, at the time of photographing a subject to be examined by the image pickup unit 10.

As described so far, the camera 1 of the present embodiment is configured to always rotate the rotary cover 3, reduce the exposure time of the cover lens 14 of the image pickup unit 10 that captures a subject image to be examined, that is, cause the cover lens 14 to be exposed only when capturing the subject image to be examined and provide the rotary cover 3 with the multi-bladed fan 20 for generating the airflow W, and thereby reduces the likelihood of lens fogging and of dirt or the like sticking to the cover lens 14 and allows the image pickup unit 10 to always obtain a clear observed image.

Furthermore, since the opening 3a of the rotary cover 3 matches the cover lens 14 which is an observation window in synchronization with the timing of the frame rate of the image pickup unit 10, the field of view of the camera 1 is not obstructed and any unnecessary configuration, that is, the inner surface of the rotary cover 3 is never included in the photographed image. Moreover, since the multi-bladed fan 20 made up of the plurality of fan blades 5 provided in the rotary cover 3 is disposed outside the range of field of view (image-pickup field of view) of the image pickup unit 10, the field of view is never obstructed.

Although a configuration has been described above where there is one opening 3a of the rotary cover 3, the present invention is not limited to this, but a plurality of openings 3a may be provided in the rotary cover 3 and the control section 7 may drive/control the motor 8 so that the number of revolutions of the rotary cover 3 matches the timing of frame rate of the image pickup unit 10 according to the number of openings 3a. That is, whether the number of openings 3a is one or plural, any configuration may be acceptable as long as the rotation of the rotary cover 3 is controlled to determine a position where the opening 3a matches the cover lens 14 according to the timing of the frame rate of the image pickup unit 10.

Furthermore, even when the camera 1 is not used, if the cover lens 14 of the image pickup unit 10 is moved to a position where the cover lens 14 is covered with the rotary cover 3 so as not to be exposed, it is possible to prevent dirt from sticking to the cover lens 14.

(Second Embodiment)

Next, a second embodiment of the camera set up in the abdominal cavity, which is a medical instrument according to the present invention, will be described below using FIG. 6 and FIG. 7. In the following descriptions, the same components as those of the camera set up in the abdominal cavity of the aforementioned first embodiment will be assigned the same reference numerals and detailed descriptions of those components and operations/effects will be omitted.

Figure 6:
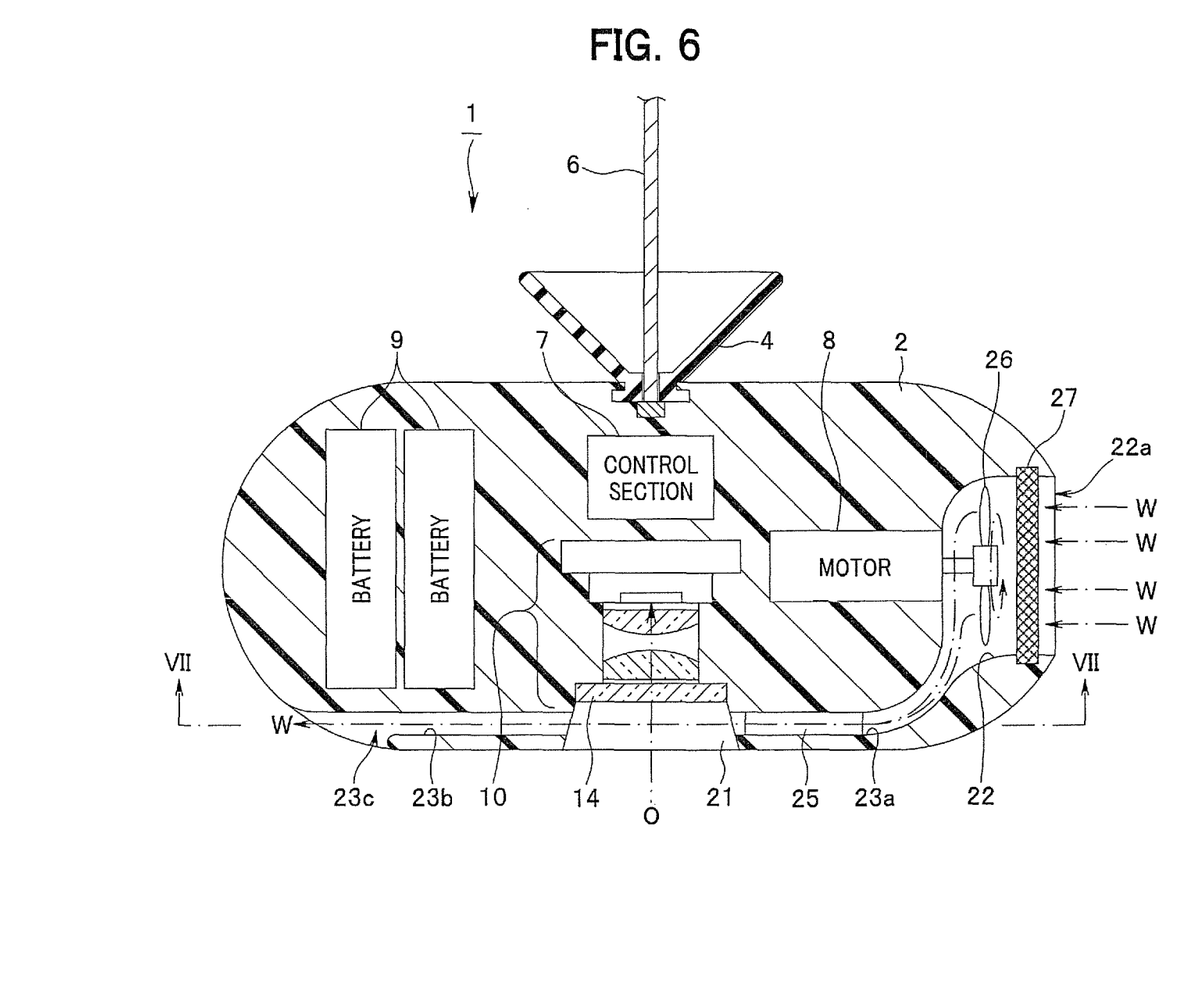
FIG. 6 is a cross-sectional view illustrating a configuration of a camera set up in the abdominal cavity according to a second embodiment.
Figure 7:
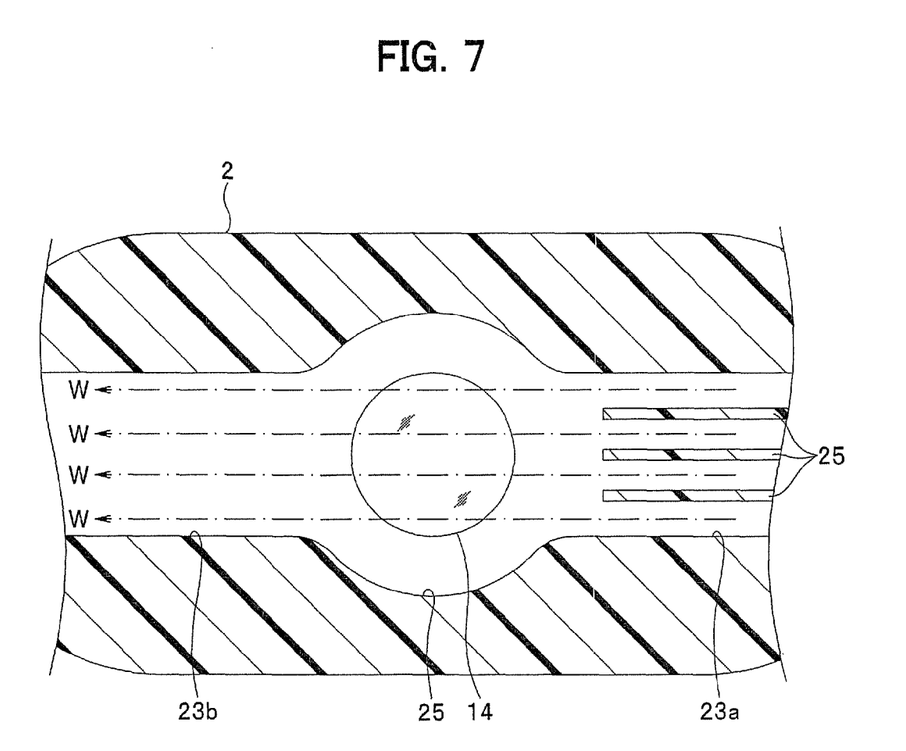
FIG. 7 is a cross-sectional view along the line VII-VII of FIG. 6 according to the second embodiment.

As shown in FIG. 6 and FIG. 7, a camera set up in the abdominal cavity (hereinafter also simply referred to as "camera") 1 of the present embodiment has a configuration in which a fan propeller 26 as an axial-flow fan which is airflow generating means (airflow generating section) for generating an airflow W on the surface of the cover lens 14 of the image pickup unit 10 in the camera body 2 is attached to the motor 8, located outside the range of field of view (image-pickup field of view) of the image pickup unit 10. Instead of the fan propeller 26 being driven by the motor 8, a fan motor which is a merge of a fan and an electric motor or the like may also be used as the airflow generating means (airflow generating section) incorporated in the camera body 2.

The fan propeller 26 is disposed in a space 22 formed outside the range of field of view (image-pickup field of view) of the image pickup unit 10 formed in the camera body 2. The space 22 has an opening on one side of the camera body 2 and this opening constitutes an inlet port 22a of the present embodiment. A filter 27 for removing humidity, dirt or the like is provided in the space 22 of the camera body 2 in the vicinity of the inlet port 22a.

Furthermore, an opening 21 which causes the cover lens 14 serving as an observation window of the image pickup unit 10 to be exposed is formed at the bottom of the camera body 2. The opening 21 communicates with an air supply path 23a and an exhaust path 23b which become two airflow paths formed in the camera body 2, constituting an airflow outlet of the present embodiment.

The air supply path 23a communicates with the space 22. The air supply path 23a is provided with a plurality of (here, three) rectification plates 25 in the longitudinal direction of the camera body 2 (see FIG. 7).

The exhaust path 23b is formed in line with the air supply path 23a with which the exhaust path 23b communicates via the opening 21 and has an opening at the other end of the camera body 2. This opening constitutes an exhaust port 23c of the present embodiment.

In the camera 1 of the present embodiment configured as shown above, the fan propeller 26 is driven to rotate by the motor 8 and the gas is thereby taken into the space 22 from the inlet port 22a. The filter 27 removes humidity, dirt or the like from the gas.

That is, an airflow W is generated in the camera body 2 by a gas taken into the space 22 through the fan propeller 26 driven by the motor 8, which is airflow generating means (airflow generating section). The airflow W flows from the space 22 into the air supply path 23a and is made to pass over the surface of the cover lens 14 of the image pickup unit 10 exposed at the opening 21. In this case, the airflow W is linearly rectified by the rectification plate 25 provided in the air supply path 23a and passes over the surface of the cover lens 14 of the image pickup unit 10.

The airflow W then flows into the exhaust path 23b that communicates with the opening 21 and the gas is exhausted from the exhaust port 23c to the abdominal cavity 101 which is outside. Not all the gas sent from the air supply path 23a to the opening 21 flows into the exhaust path 23b, but part thereof is exhausted from the opening 21.

As described above, in the camera 1 of the present embodiment, the gas taken into the space 22 of the camera body 2 through the fan propeller 26 forms a so-called air curtain, passes through the opening 21 and is exhausted from the exhaust port 23c via the exhaust path 23b. Therefore, the wind force blows off dirt by blood, mucous membrane or the like scattering from the treated diseased part and smoke or the like generated during treatment of the diseased part using a high frequency treatment device. This prevents dirt or the like from approaching the surface of the cover lens 14, thereby prevents the lens from fogging or dirt from sticking to the surface of the cover lens 14. Here, the fan propeller 26 is also always driven to rotate when the camera 1 is driven, that is, at the time of photographing a subject to be examined by the image pickup unit 10.

As described so far, the camera 1 of the present embodiment also has effects similar to those of the first embodiment, and by generating the airflow W through the rotation of the fan propeller 26, the camera 1 reduces the likelihood of lens fogging and of dirt or the like sticking to the cover lens 14 and allows the image pickup unit 10 to always obtain a clear observed image.

(Third Embodiment)

Next, a third embodiment of the camera set up in the abdominal cavity, which is a medical instrument according to the present invention, will be described below using FIG. 8 and FIG. 9. In the following descriptions, the same components as those of the camera set up in the abdominal cavity of the aforementioned first embodiment will be assigned the same reference numerals and detailed descriptions of those components and operations/effects will be omitted.

Figure 8:
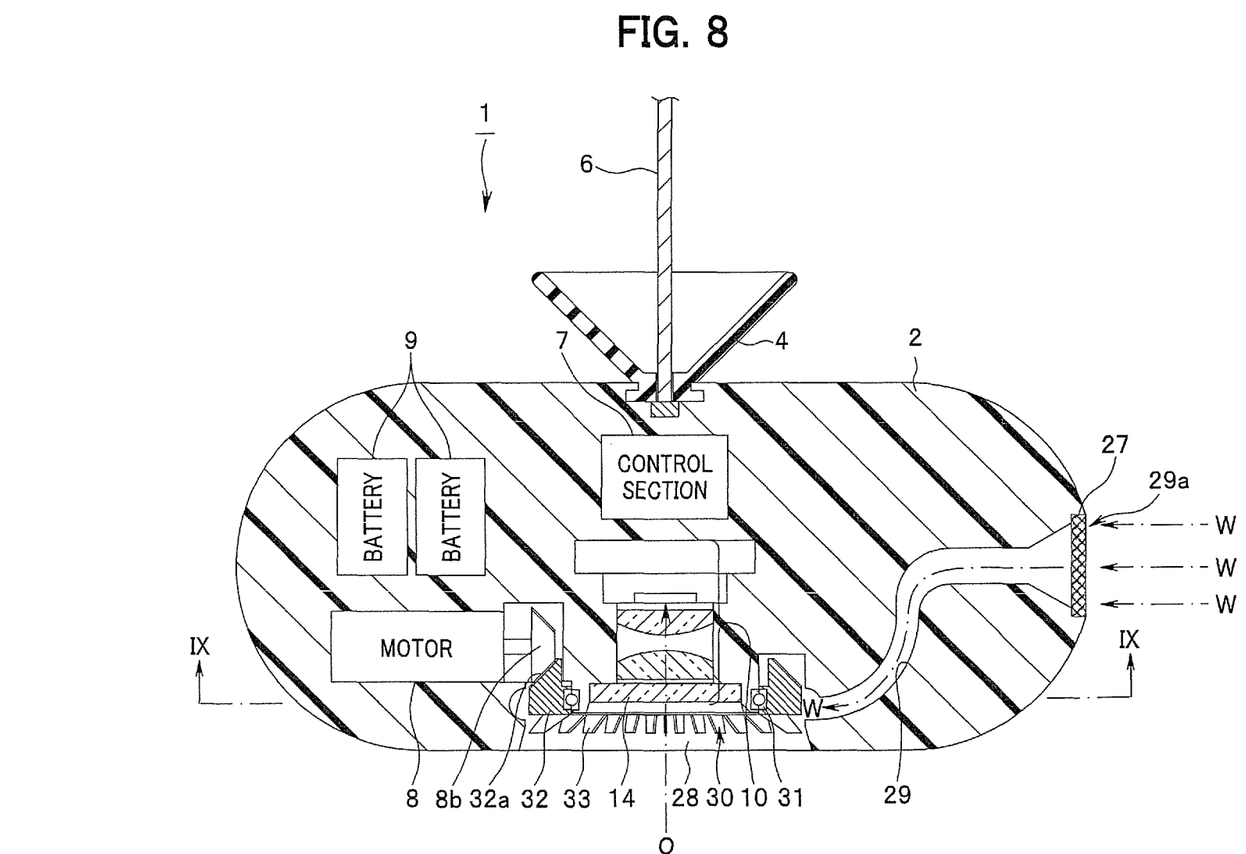
FIG. 8 is a cross-sectional view illustrating a configuration of a camera set up in the abdominal cavity according to a third embodiment.
Figure 9:
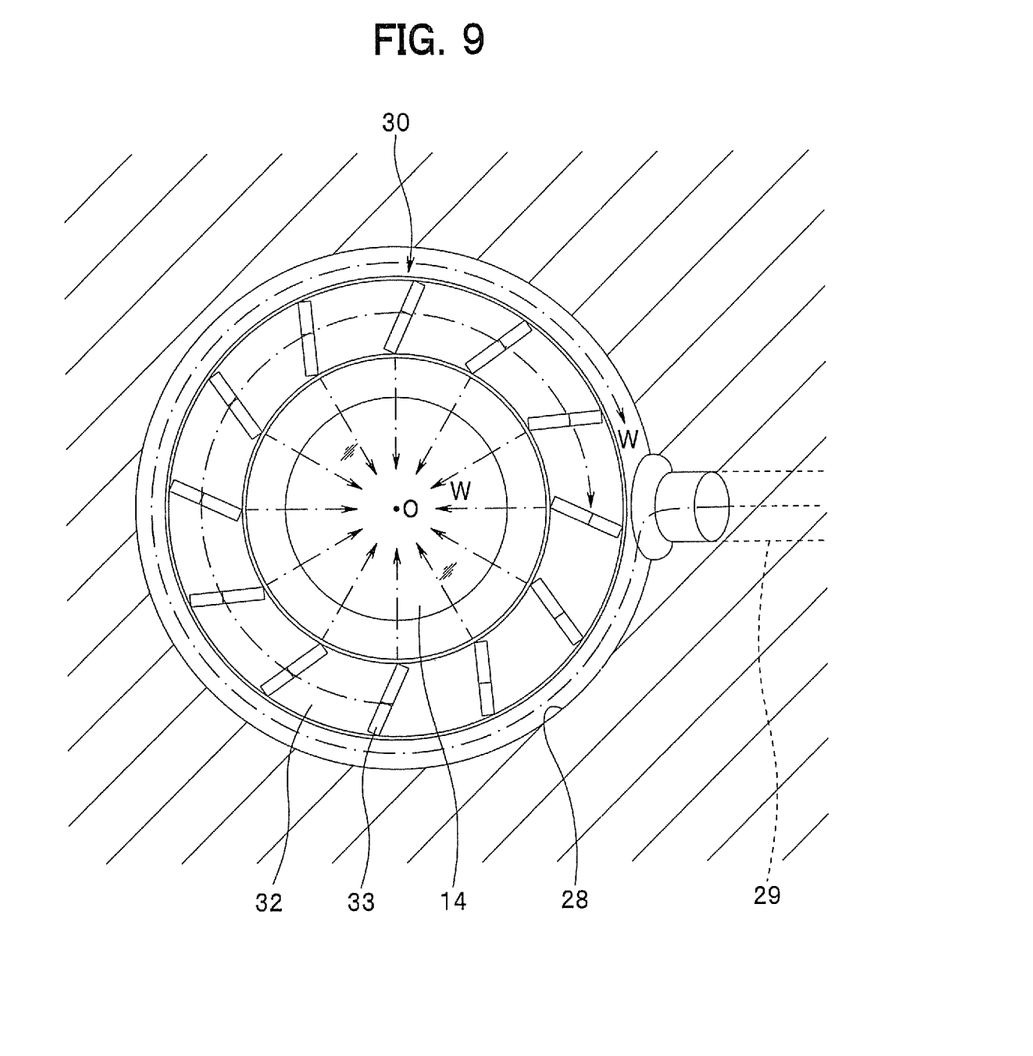
FIG. 9 is a cross-sectional view along the line IX-IX of FIG. 8 according to the third embodiment.

As shown in FIG. 8 and FIG. 9, a camera set up in the abdominal cavity (hereinafter also simply referred to as "camera") 1 of the present embodiment has a configuration in which a plurality of fan blades 33 making up a multi-bladed fan 30 which is airflow generating means (airflow generating section) for generating an airflow W towards the surface of the cover lens 14 of the image pickup unit 10 in the camera body 2 are disposed outside the range of field of view (image-pickup field of view) of the image pickup unit 10 so as to rotate around the cover lens 14.

The plurality of fan blades 33 are disposed around the cover lens 14 of the image pickup unit 10 of the camera body 2 on one side of a rotary ring body 32 rotatably supported by a bearing 31 so as to surround the cover lens 14. The rotary ring body 32 is disposed at an opening 28 of the camera body 2 installed such that the cover lens 14, which is an observation window, is exposed.

Furthermore, the outer edge on the other surface side positioned in the camera body 2 of the rotary ring body 32 is formed into a conical shape and a gear groove 32a having teeth is formed on the conical surface thereof. The gear groove 32a meshes with a gear 8b which is driven to rotate by the motor 8. That is, the rotary ring body 32 and the gear 8b constitute a bevel gear. Thus, the rotary ring body 32 is driven to rotate around the optical axis O of the image pickup unit 10 by the gear 8b of the motor 8.

The opening 28 communicates with an inlet path 29 formed in the camera body 2, constituting an airflow outlet of the present embodiment. The inlet path 29 has an opening on one side of the camera body 2. The opening constitutes an inlet port 29a in the present embodiment. Furthermore, a filter 27 for removing humidity, dirt or the like is disposed at the inlet port 29a.

That is, when the rotary ring body 32 of the camera 1 rotates, the gas in the abdominal cavity 101 is suctioned from the inlet port 29a through the plurality of fan blades 33 making up the multi-bladed fan 30 into the inlet path 29. The suctioned gas in the inlet path 29 is exhausted from the opening 28 to the abdominal cavity 101 which is outside. Here, the filter 27 also removes humidity, dirt or the like from the suctioned gas.

That is, an airflow W passing through the cover lens 14 of the image pickup unit 10 and exhausted from the opening 28 is also generated in the camera 1 of the present embodiment (see FIG. 9).

As described so far, in the camera 1 of the present embodiment, a gas suctioned into the inlet path 29 of the camera body 2 by the plurality of fan blades 33 provided in the rotary ring body 32 forms a so-called air curtain and is exhausted from the opening 28. Therefore, in the present embodiment, the wind force of the airflow W blows off dirt by blood, mucous membrane or the like scattering from the treated diseased part and smoke or the like generated during treatment of the diseased part using a high frequency treatment device, thus preventing dirt or the like from approaching the surface of the cover lens 14, thereby preventing the lens from fogging or dirt from sticking to the surface of the cover lens 14. Here, the rotary ring body 32 provided with the plurality of fan blades 33 is also always driven to rotate when the camera 1 is driven, that is, at the time of photographing a subject to be examined by the image pickup unit 10.

As described so far, the camera 1 of the present embodiment also has effects similar to those of the first embodiment, and by generating the airflow W through the rotation of the plurality of fan blades 33 provided in the rotary ring body 32, the camera 1 reduces the likelihood of lens fogging and of dirt or the like sticking to the cover lens 14 and allows the image pickup unit 10 to always obtain a clear observed image. Furthermore, the multi-bladed fan 30 made up of the plurality of fan blades 5 provided in the rotary ring body 32 is disposed outside the range of field of view (image-pickup field of view) of the image pickup unit 10, and therefore the multi-bladed fan 30 never obstructs the field of view.

(Fourth Embodiment)

Next, a fourth embodiment of the camera set up in the abdominal cavity, which is a medical instrument according to the present invention, will be described below using FIG. 10 to FIG. 15. In the following descriptions, the same components as those of the camera set up in the abdominal cavity of the aforementioned first embodiment will be assigned the same reference numerals and detailed descriptions of those components and operations/effects will be omitted.

Figure 10:
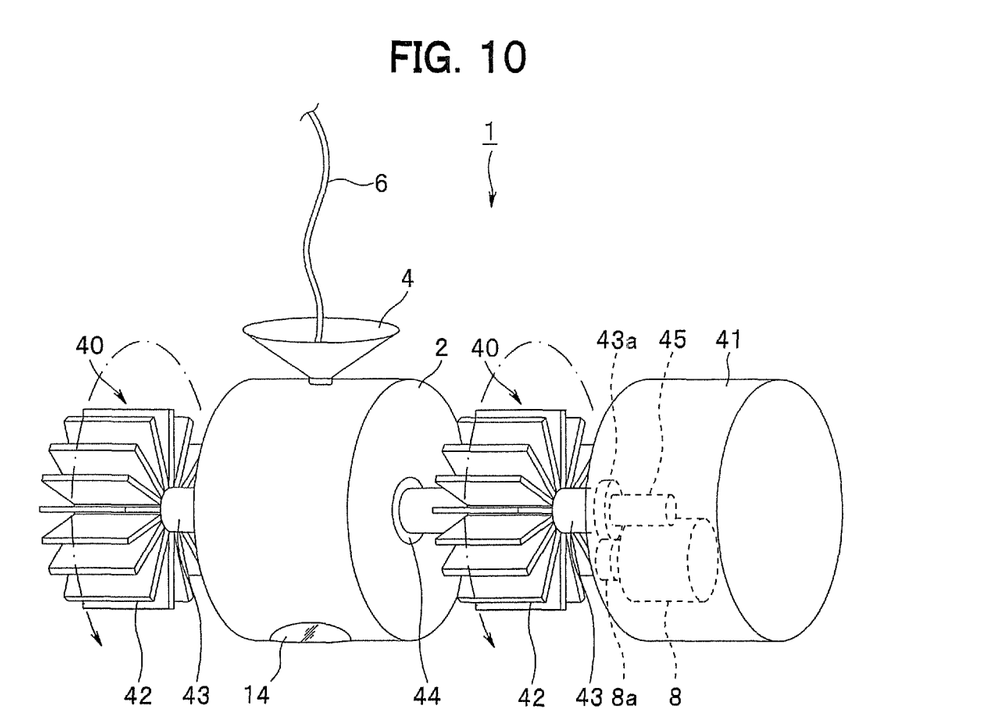
FIG. 10 is a perspective view illustrating a configuration of a camera set up in the abdominal cavity according to a fourth embodiment.
Figure 11:
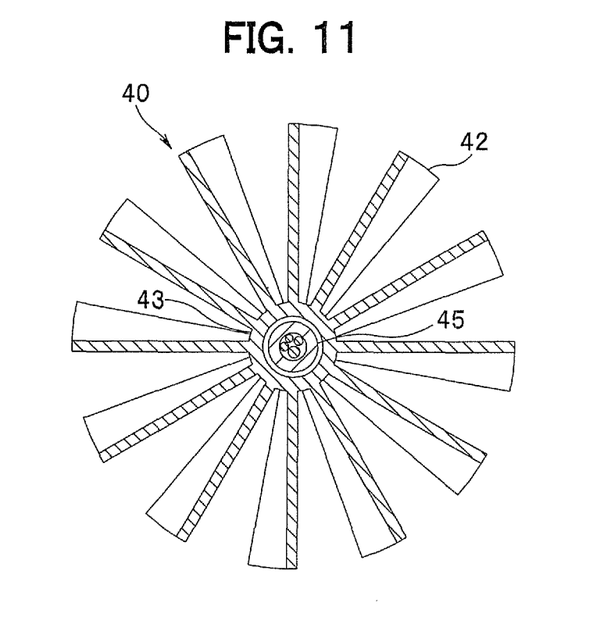
FIG. 11 is a cross-sectional view illustrating a multi-bladed fan according to the fourth embodiment.
Figure 12:
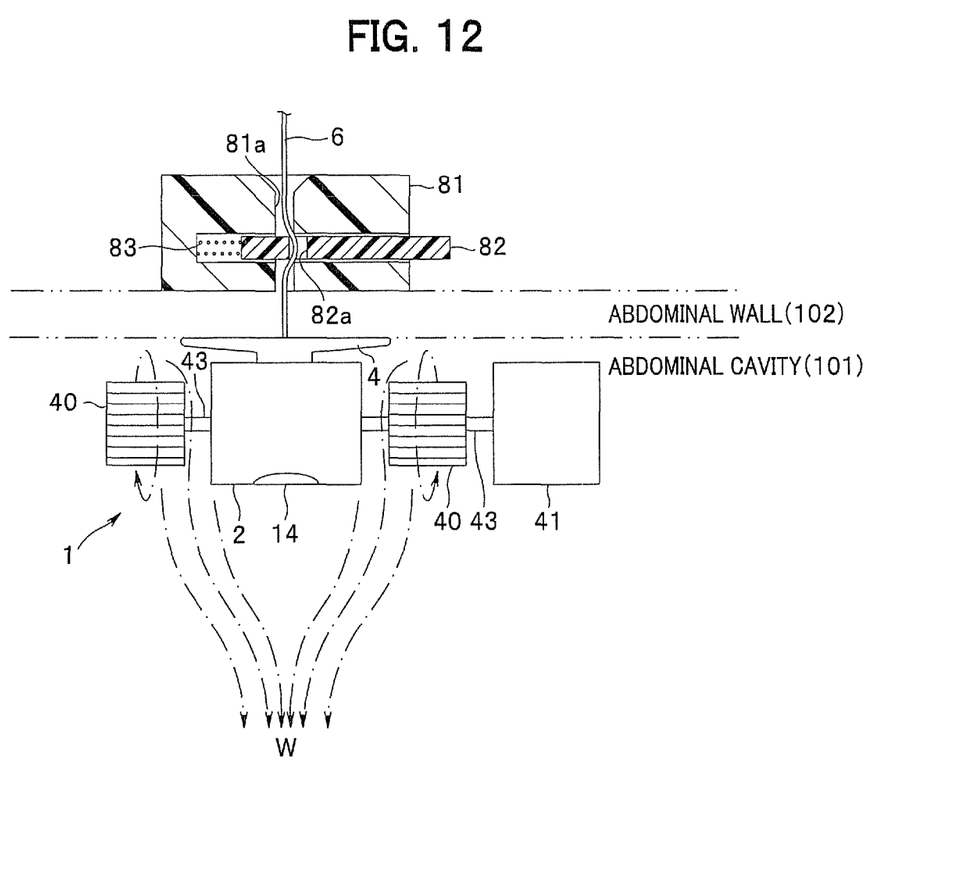
FIG. 12 is a partial cross-sectional view illustrating the camera set up in the abdominal cavity according to the fourth embodiment installed in the abdominal cavity.

As shown in FIG. 10 to FIG. 12, a camera set up in the abdominal cavity (hereinafter also simply referred to as "camera") 1 of the present embodiment has a configuration in which a plurality of fan blades 42 making up a multi-bladed fan 40 which is airflow generating means (airflow generating section) for generating an airflow W around the surface of the cover lens 14 of the image pickup unit 10 is disposed outside the range of field of view (image-pickup field of view) of the image pickup unit 10. The camera 1 has a configuration having two multi-bladed fans 40 that is disposed so as to extend from both sides of the camera body 2 having a columnar outline.

Furthermore, the camera 1 is provided with a drive unit 41 having a substantially columnar outline disposed so as to sandwich the one multi-bladed fan 40 between itself and the camera body 2. The drive unit 41 incorporates a motor 8 to rotate the two multi-bladed fans 40, and a control section 7 and a battery 9 (both are not shown here).

A gear 8a driven by the motor 8 meshes with a spur gear 43a formed on a shaft body 43 which is integrally formed with the two multi-bladed fans 40. Thus, the two multi-bladed fans 40 receive the drive force of the motor 8 and rotate around the shaft body 43.

The shaft body 43 is cylindrical and rotatably supported by a bearing 44 provided at the center of both sides of the camera body 2. Furthermore, though not shown, the shaft body 43 is also rotatably supported by the drive unit 41 via a bearing or the like. The gear 43a provided at one end of the shaft body 43 is disposed in the drive unit 41 and meshes with the gear 8a of the motor 8.

A connecting shaft 45 for connecting and fixing the camera body 2 and the drive unit 41 is inserted in the shaft body 43. The connecting shaft 45 is also cylindrical and incorporates various electric communication wirings for electric connections with the image pickup unit 10 of the camera body 2 and the control section 7 and the battery 9 in the drive unit 41 (see FIG. 11).

When the camera 1 of the present embodiment configured as shown above is installed in the abdominal cavity 101 as shown in FIG. 12, the two multi-bladed fans 40 rotate and generate an airflow W. Since the camera 1 is fixed to the abdominal wall 102 and the top of the camera 1 is shielded, the airflow W is generated so that the gas flows toward the subject (subject to be examined), that is, downward.

Therefore, in the camera 1 of the present embodiment, the wind force of the airflow W also blows off dirt by blood, mucous membrane or the like scattering from the treated diseased part, smoke or the like generated during treatment of the diseased part using a high frequency treatment device, thus preventing dirt or the like from approaching the surface of the cover lens 14, thereby preventing the lens from fogging or dirt from sticking to the surface of the cover lens 14.

As will be described in the following modification examples, the camera body 2 may also have various configurations in which the airflow W generated through the rotation of the multi-bladed fan 40 flows in the vicinity of the cover lens 14 of the image pickup unit 10.

(First Modification Example)

Figure 13:
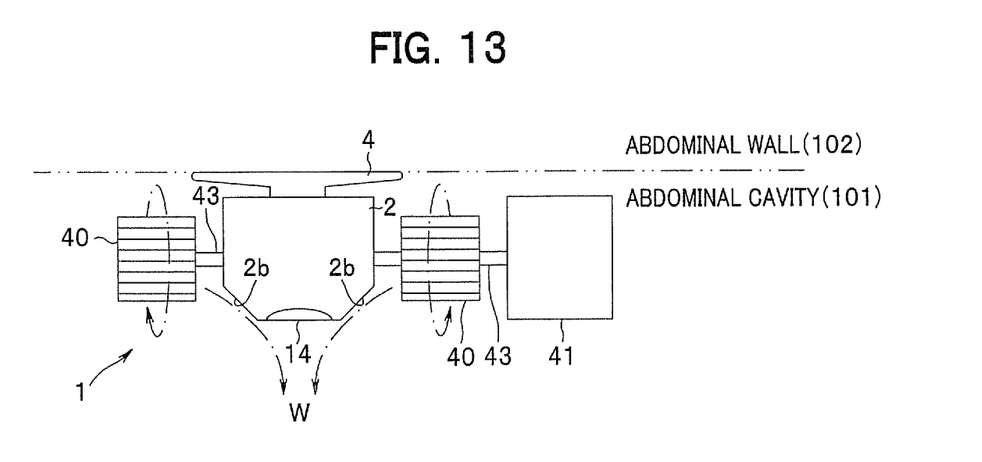
FIG. 13 is a diagram illustrating a configuration of a camera set up in the abdominal cavity according to a first modification example according to the fourth embodiment.

As shown in FIG. 13, both sides of the camera body 2 may be chipped and a tapered surface 2b toward the cover lens 14 may be formed so that the airflow W generated through the rotation of the multi-bladed fan 40 flows toward the cover lens 14 disposed at the bottom.

(Second Modification Example)

Figure 14:
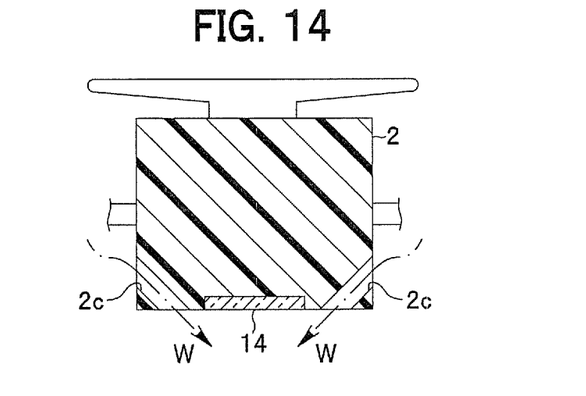
FIG. 14 is a partial cross-sectional view illustrating a configuration of a camera set up in the abdominal cavity according to a second modification example according to the fourth embodiment.

As shown in FIG. 14, vent ports 2c may be formed from both sides downward to the cover lens 14 in the camera body 2 so that the airflow W generated through the rotation of the multi-bladed fan 40 flows toward the cover lens 14 disposed at the bottom.

(Third Modification Example)

Figure 15:
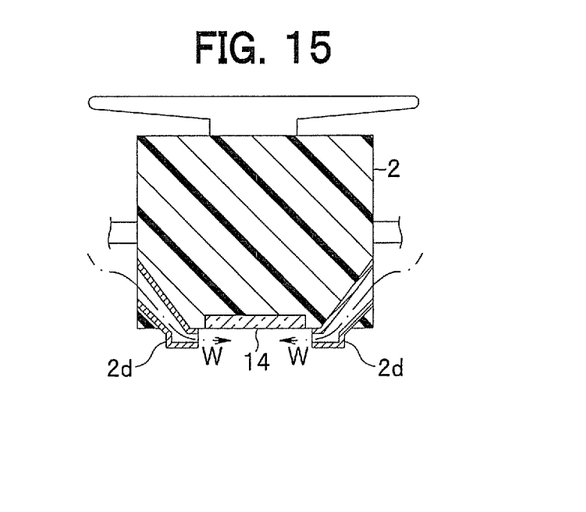
FIG. 15 is a partial cross-sectional view illustrating a configuration of a camera set up in the abdominal cavity according to a third modification example according to the fourth embodiment.

As shown in FIG. 15, the camera body 2 may also be provided with vent nozzles 2d in holes formed from both sides downward to the cover lens 14 so that the airflow W generated through the rotation of the multi-bladed fan 40 flows toward the cover lens 14 disposed at the bottom.

The opening at the distal end of the vent nozzle 2d, that is, the exhaust outlet from which the gas is exhausted is formed so as to face the surface of the cover lens 14.

As described so far, by adopting the various configurations of these modification examples, the airflow W flows around the surface of the cover lens 14, forms a so-called air curtain and the wind force of the airflow W blows off dirt by blood, mucous membrane or the like scattering from the treated diseased part and smoke or the like generated during treatment of the diseased part using a high frequency treatment device, thus preventing dirt or the like from approaching the surface of the cover lens 14, thereby preventing the lens from fogging or dirt from sticking to the surface of the cover lens 14.

(Fifth Embodiment)

Next, a fifth embodiment of the camera set up in the abdominal cavity, which is a medical instrument according to the present invention, will be described below using FIG. 16 and FIG. 17. In the following descriptions, the same components as those of the camera set up in the abdominal cavity of the aforementioned first embodiment will be assigned the same reference numerals and detailed descriptions of those components and operations/effects will be omitted.

Figure 16:
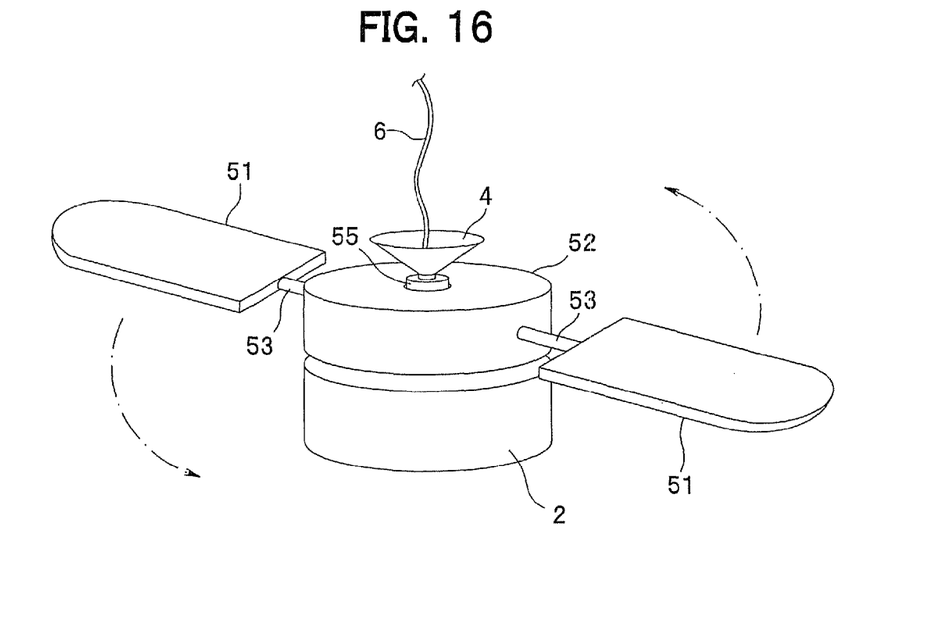
FIG. 16 is a perspective view illustrating a configuration of a camera set up in the abdominal cavity according to a fifth embodiment.
Figure 17:
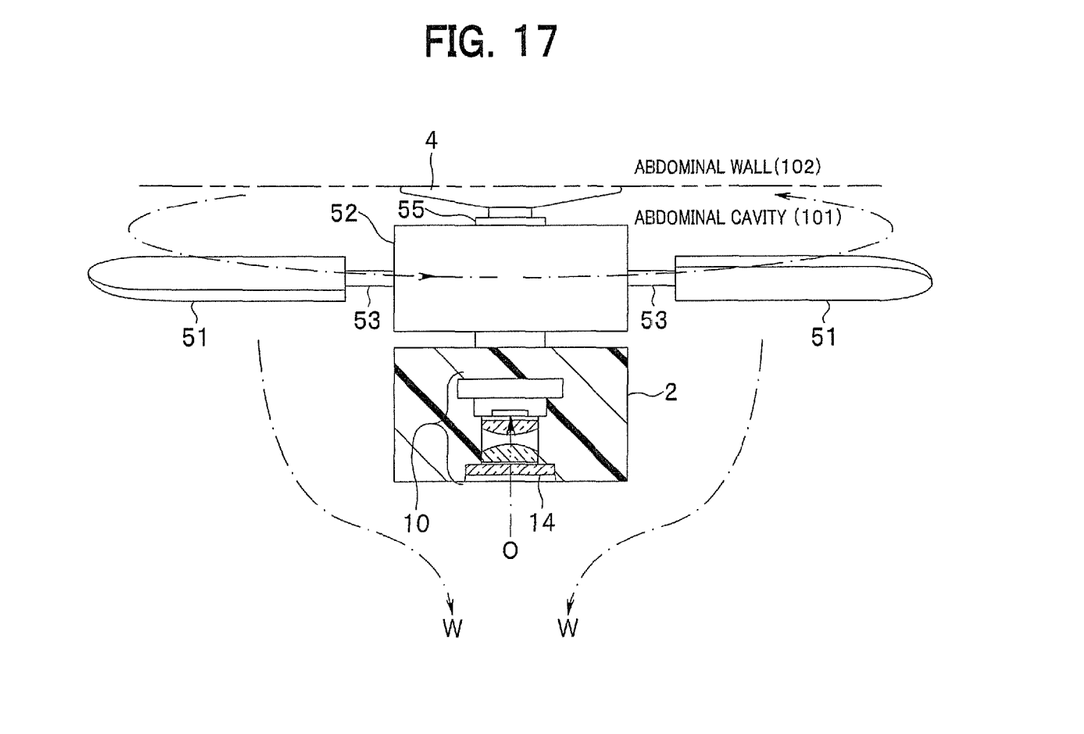
FIG. 17 is a partial cross-sectional view illustrating the camera set up in the abdominal cavity according to the fifth embodiment installed in the abdominal cavity.

As shown in FIG. 16 and FIG. 17, a camera set up in the abdominal cavity (hereinafter also simply referred to as "camera") 1 of the present embodiment has two fan propellers 51 which are airflow generating means (airflow generating sections) for generating an airflow W around the surface of the cover lens 14 of the image pickup unit 10 rotatably arranged with respect to the camera body 2 at positions outside the range of field of view (image-pickup field of view) of the image pickup unit 10.

The two fan propellers 51 are connected to the outer circumferential face of a cylindrical body of revolution 52 so as to extend in directions opposite to each other via a bar-shaped connecting section 53. The body of revolution 52 is driven to rotate by a motor (not shown) disposed on a cylindrical shaft 55 around the longitudinal axis of the cylindrical shaft 55, on the top surface of which the suction cup 4 is fixed and the bottom of which is connected to the camera body 2. Though not shown, the wire 6 is inserted in the cylindrical shaft 55 and one end thereof is connected to the camera body 2.

When the camera 1 of the present embodiment configured as shown above is installed in the abdominal cavity 101, the airflow W is generated by rotating the two fan propellers 51 as shown in FIG. 17. Since the camera 1 is fixed to the abdominal wall 102 and the top of the camera 1 is shielded as in the case of the fourth embodiment, the airflow W is generated so as to flow toward the subject (subject to be examined), that is, downward.

Therefore, in the camera 1 of the present embodiment, the wind force of the airflow W also blows off dirt by blood, mucous membrane or the like scattering from the treated diseased part and smoke or the like generated during treatment of the diseased part using a high frequency treatment device, thus preventing dirt or the like from approaching the surface of the cover lens 14, thereby preventing the lens from fogging or dirt from sticking to the surface of the cover lens 14.

The camera body 2 may also have various configurations in which the airflow W generated through the rotation of the fan propeller 51 flows in the vicinity of the cover lens 14 of the image pickup unit 10 as in the case of the various modification examples described in the fourth embodiment.

The medical instrument according to the above described embodiments prevents adherents from sticking to the observation window of the observation apparatus without obstructing the field of view and allows a clear observed image to be obtained.

What is claimed is:

1. A medical instrument for observing an interior of a subject to be examined, comprising:
   an image pickup unit incorporated in a medical instrument body, for picking up an image of the subject to be examined from an observation window;
   a rotary cover having a cylindrical shape and provided rotatably on an outer circumferential portion of the medical instrument body so as to cover the image pickup unit, the rotary cover being provided with an inlet port, and an opening on the outer circumferential portion of the rotary cover for exposing the image pickup unit;
   a multi-bladed fan provided on an inner perimeter of the rotary cover and configured to take in air from the inlet port and exhaust an airflow for preventing adherents from sticking to the observation window by rotation of the rotary cover;
   a fixing unit for indwelling and fixing the medical instrument body inside the subject to be examined; and
   a drive unit incorporated in the medical instrument body, for driving the rotary cover to be rotated,
   wherein the rotary cover rotates and moves to a position where the opening aligns with the observation window in accordance with a timing of a frame rate of the image pickup unit.

2. The medical instrument according to claim 1, wherein the multi-bladed fan is provided in the vicinity of the inlet port.

* * * * *